United States Patent
Kroll et al.

(10) Patent No.: US 7,203,550 B2
(45) Date of Patent: Apr. 10, 2007

(54) IMPLANTABLE MEDICAL DEVICE WITH A CURRENT GENERATED FOR INFECTION CONTROL

(75) Inventors: Mark Kroll, Simi Valley, CA (US); Johan Eckerdal, Knivsta (SE); Martin Obel, Danderyd (SE); Eva Micski, Huddinge (SE)

(73) Assignee: St. Jude Medical AB, Jarfalla (SE)

( * ) Notice: Subject to any disclaimer, the term of this patent is extended or adjusted under 35 U.S.C. 154(b) by 502 days.

(21) Appl. No.: 10/468,867

(22) PCT Filed: Feb. 26, 2002

(86) PCT No.: PCT/SE02/00345

§ 371 (c)(1),
(2), (4) Date: Aug. 22, 2003

(87) PCT Pub. No.: WO02/068049

PCT Pub. Date: Sep. 6, 2002

(65) Prior Publication Data

US 2004/0098055 A1 May 20, 2004

(30) Foreign Application Priority Data

Feb. 27, 2001 (SE) .................................. 0100669

(51) Int. Cl.
*A61N 1/00* (2006.01)
*A61B 19/00* (2006.01)
*B65B 55/02* (2006.01)

(52) U.S. Cl. .................. 607/63; 607/2; 607/3; 607/36; 607/50; 607/75; 607/116; 607/120; 607/4; 607/5; 607/9; 128/898; 53/425

(58) Field of Classification Search .................. 607/2, 607/3, 36, 50, 63, 75, 116, 120, 4, 5, 9; 128/898; 53/425

See application file for complete search history.

(56) References Cited

U.S. PATENT DOCUMENTS

| | | |
|---|---|---|
| 4,886,505 A | 12/1989 | Haynes et al. |
| 5,312,813 A | 5/1994 | Costerton et al. |
| 5,409,467 A | 4/1995 | Raad et al. |

(Continued)

OTHER PUBLICATIONS

"Prevention and Control of Bacterial Infections Associated with Medical Devices," Khoury et al., ASAIO Journal, 1992, pp. M174-M178.

*Primary Examiner*—Robert E. Pezzuto
*Assistant Examiner*—Natasha Patel
(74) *Attorney, Agent, or Firm*—Schiff Hardin LLP

(57) ABSTRACT

In a cardiac stimulating device, an infection control current is generated and applied to a subject in whom a medical device is implanted by completing a circuit including an entirely electrically conductive exterior of a housing of the device, an electrode carried by an electrode lead of the device, and an electrically conductive surface of a proximal portion of the electrode lead, extending from the housing to a location, after implantation, situated beyond entry of the electrode lead into the venous system and before entry of the electrode lead into the superior vena cava. The infection control current can be a current with a square waveform, and the circuit can be completed at selected times, such as only during the refractory period of the subject's heart.

32 Claims, 5 Drawing Sheets

U.S. PATENT DOCUMENTS

| | | |
|---|---|---|
| 5,462,644 A | 10/1995 | Woodson |
| 5,510,766 A | 4/1996 | Harman et al. |
| 5,713,926 A | 2/1998 | Hauser et al. |
| 5,814,076 A | 9/1998 | Brownlee |
| 6,258,249 B1 | 7/2001 | Simpson |
| 6,282,444 B1 * | 8/2001 | Kroll et al. .................... 607/3 |
| 6,295,474 B1 * | 9/2001 | Munshi ....................... 607/121 |

* cited by examiner

IMPLANTABLE MEDICAL DEVICE WITH A CURRENT GENERATED FOR INFECTION CONTROL

BACKGROUND OF THE INVENTION

1. Field of the Invention

The present invention relates generally to an apparatus for killing microorganisms which may form in a biofilm on surfaces of implanted devices and, more particularly, to such an apparatus used with a cardiac stimulation device, e.g., a cardioverter-defibrillator (ICD), pacemaker or the like.

2. Description of the Prior Art

Infections which may occur with pacemaker/ICD devices are relatively untreatable without device removal since the bacteria live in a biofilm on the device which blocks antibiotics. When the biofilm of such an implantable device becomes infected, it is almost universally impossible to treat the infection with systemic antibiotics. The standard medical procedure is to explant the device, leading to additional costs, risks and discomfort to the patient.

The reason that device infections cannot be treated by systemic antibiotics is that the biofilm protects the bacteria from systemic antibiotics and allows them to tolerate levels of antibiotics that are several orders of magnitude above that which can safely be given to a patient.

To overcome this tolerance to antibiotics, the use of electrical fields to kill bacteria in the biofilm has been investigated and discussed. Exemplary patents include U.S. Pat. Nos. 5,312,813; 5,409,467; and 5,462,644.

SUMMARY OF THE INVENTION

The present invention is directed to an apparatus for treating an infection which may occur in the biofilm which surrounds an implanted cardiac stimulation device, e.g., a cardioverter-defibrillator (ICD) or a pacemaker. Such infections are relatively untreatable by conventional antibiotics treatments. Thus, explanting of the implanted devices may be required. Accordingly, the present apparatus provides an electrical treatment that enables a biocide, i.e., an antibiotic, to successfully treat the infection within the biofilm and thus avoid the necessity to explant the device. Furthermore, the present invention provides this electrical treatment in a manner to not interfere with the stimulation pulses of the cardiac stimulation device.

A biofilm is a conglomerate of microbial organisms imbedded in a highly hydrated matrix of exopolymers, typically polysaccharides and other macromolecules. Unlike planktonic organisms which are relatively susceptible to antibiotics, the structural matrix established during biofilm formation can make the colonizing cells able to withstand normal treatment doses of a biocide. However, the application of a relatively low current on the order of perhaps 10–100 microamperes per square centimeter is sufficient to allow the antibiotics to penetrate the biofilm and destroy the bacteria.

In one study (ASAIO Journal 1991; 38:M174–M178, Prevention and Control of Bacterial Infections Associated with Medical Devices by Khoury et al.), the curve presented in FIG. 1 was generated. The solid line shows only a minimal reduction in the concentration of living biofilm cells after a dozen hours of the application of an antibiotic. On the other hand, by applying a low current, the number of living biofilm cells dropped by one order of magnitude every two hours.

The present invention provides an electric current to treat an infection in the surrounding biofilm of an implanted cardiac stimulation device, e.g., a cardioverter-defibrillator (ICD), pacemaker or the like. More specifically, a first coil, i.e., the SVC coil, is implanted in the region of the right atrium and a second coil, i.e., the RV coil, or other suitable electrode is implanted in the right ventricle (RV). Currents are delivered between the RV coil and from the SVC coil to the conductive case of an implanted cardiac stimulation device to treat the infection.

Currents on the order of 15 microamperes per square centimeter are considered therapeutic for this process. Due to the heterogeneities of the current in an ICD surface, for example, one must be conservative in estimating the currents. It is desirable to assume a very cautious position, that the current density in the device housing varies by 100:1 from the highest to the lowest current density. To simplify the calculations, it is further assumed that the lowest current density is $\frac{1}{10}$ of the average. Thus, an average current density of 150 microamperes per square centimeter is needed to guarantee the minimum requirement for purposes of the invention. Assuming a device having a 70 cm$^2$ surface area, this results in a treatment level of about 10 ma for the average current to the device. This average current is preferably maintained for about 10 hours (see FIG. 1) to achieve a maximum therapeutic benefit. However, a 10 ma current from an implantable coil to the case of a cardiac stimulation device is also capable of pacing the heart and thus care must be taken to not induce an arrhythmia. Accordingly, the present invention supplies an infection control current in a manner to not interfere with either the natural pacing of the heart or pacing pulses supplied or sensed by an implanted cardiac stimulation device. Accordingly, the risk of causing an arrhythmia is minimized.

In a first embodiment, the application of the infection control current is restricted to the refractory periods of portions, e.g., the atria and/or ventricles, of the cardiac muscle (i.e., the heart). Since the heart cannot be stimulated during these time periods, the heart's operation is not affected by this infection control current In a next operational mode, the infection control current is applied at a frequency that is too high to stimulate the heart.

Thus, a primary feature of the present invention is the use of electric currents to control/treat infections associated with a cardiac stimulation device without adversely effecting the operation of the cardiac stimulation device or the heart.

Another feature of the present invention is the use of the casing (housing) of the device as one of its electrodes for supplying (or sinking) the electrical current.

In a first treatment mode, the present invention is used, preferably in conjunction with a course of antibiotics, when an infection is first detected.

In a second treatment mode, the present invention can be used prophylactically following implantation of the cardiac stimulation device in conjunction with the traditionally applied antibiotic treatment that follows surgery.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DESCRIPTION OF THE PREFERRED EMBODIMENTS

The present invention is directed to an apparatus far treating an infection which may occur in the biofilm which surrounds an implanted cardiac stimulation device, e.g., a cardioverter-defibrillator (ICD) or a pacemaker. Such infections are relatively untreatable by conventional antibiotics treatments. Thus, explanting of the implanted devices may be required. Accordingly, the present apparatus provides an electrical treatment that enables a biocide, i.e., an antibiotic, to successfully treat the infection within the biofilm and thus avoid the necessity to explant the device. Furthermore, the present invention provides this electrical treatment in a manner to not interfere with the stimulation pulses of the cardiac stimulation device.

As indicated above, the present invention may be used with various types of implantable stimulation devices, including an implantable pacemaker configured to treat bradycardia and/or tachycardia, an implantable cardioverter-defibrillator (ICD), or a combination thereof. Such devices control/monitor the operations of a patient's heart.

To better understand the invention, it will first be helpful to have an understanding of the basic functions performed by exemplary implantable stimulation devices with which the invention may be used, e.g., an ICD with dual chamber coils and/or a dual-chamber pacemaker. While a dual-chamber device has been chosen for this description, this is for teaching purposes only. It is recognized that the present invention could be implemented into a single-chamber device, that one of skill in the art could readily adapt the dual-chamber device shown in FIG. 3 to perform single-chamber functionality, and that a single-chamber device is within the spirit of the invention.

Figure 1:
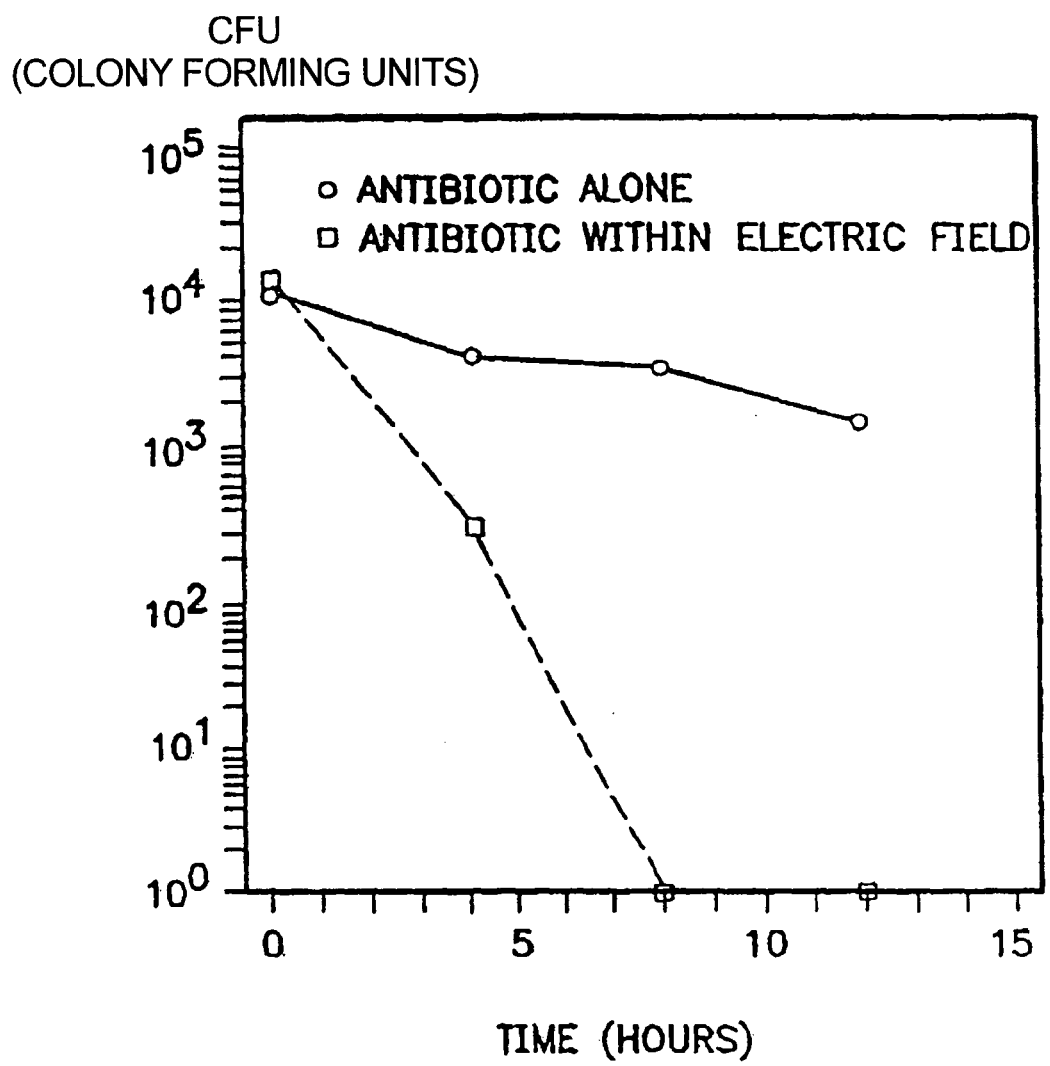
FIG. 1 is a graph comparing the success of killing biofilm cells over time with antibiotics alone as compared with antibiotics within an electric field.
Figure 2:
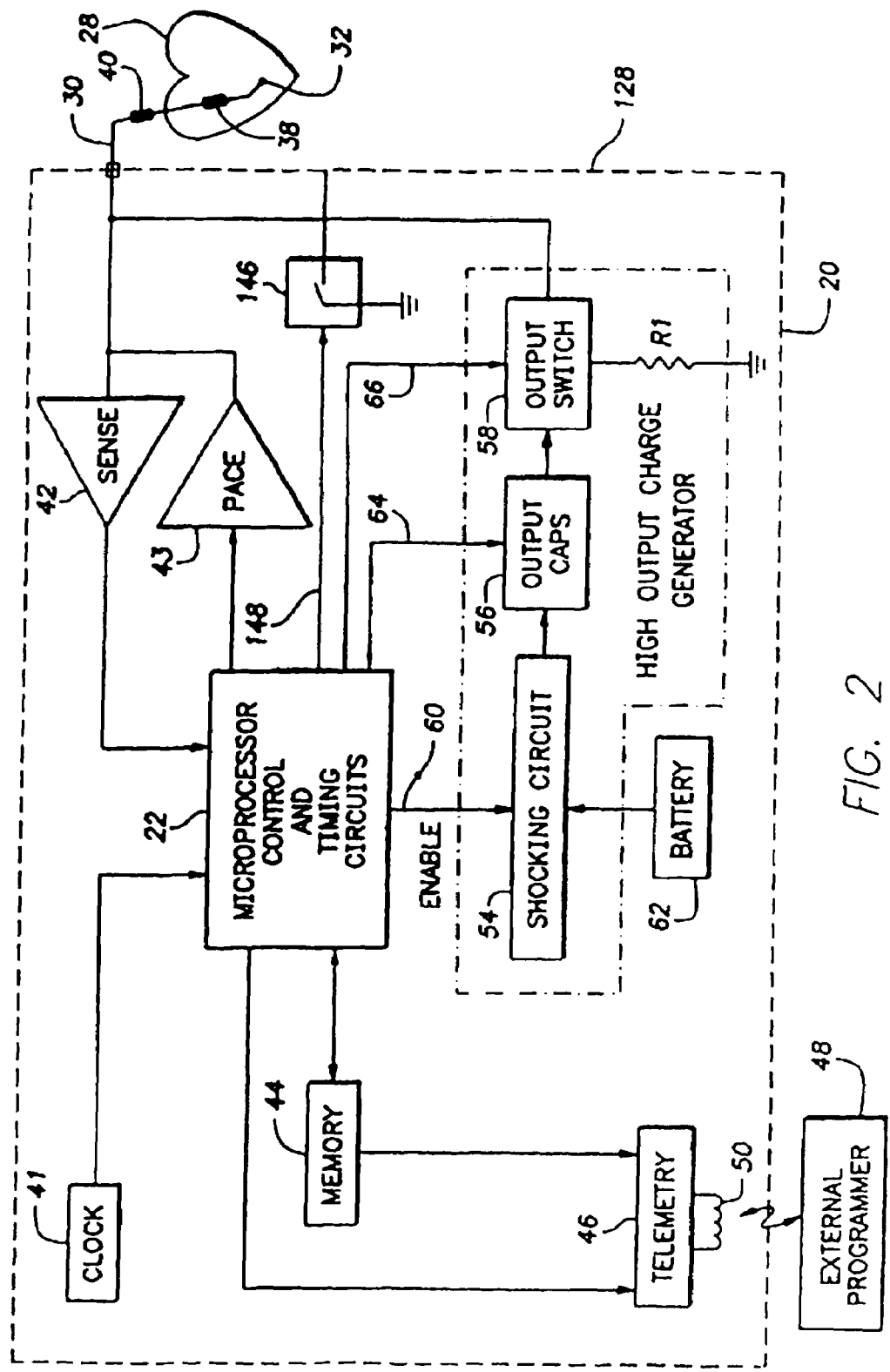
FIG. 2 shows a simplified functional block diagram of an implantable cardioverter-defibrillator (ICD), which represents one type of implantable stimulation device with which the present invention may be used.
Figure 3:
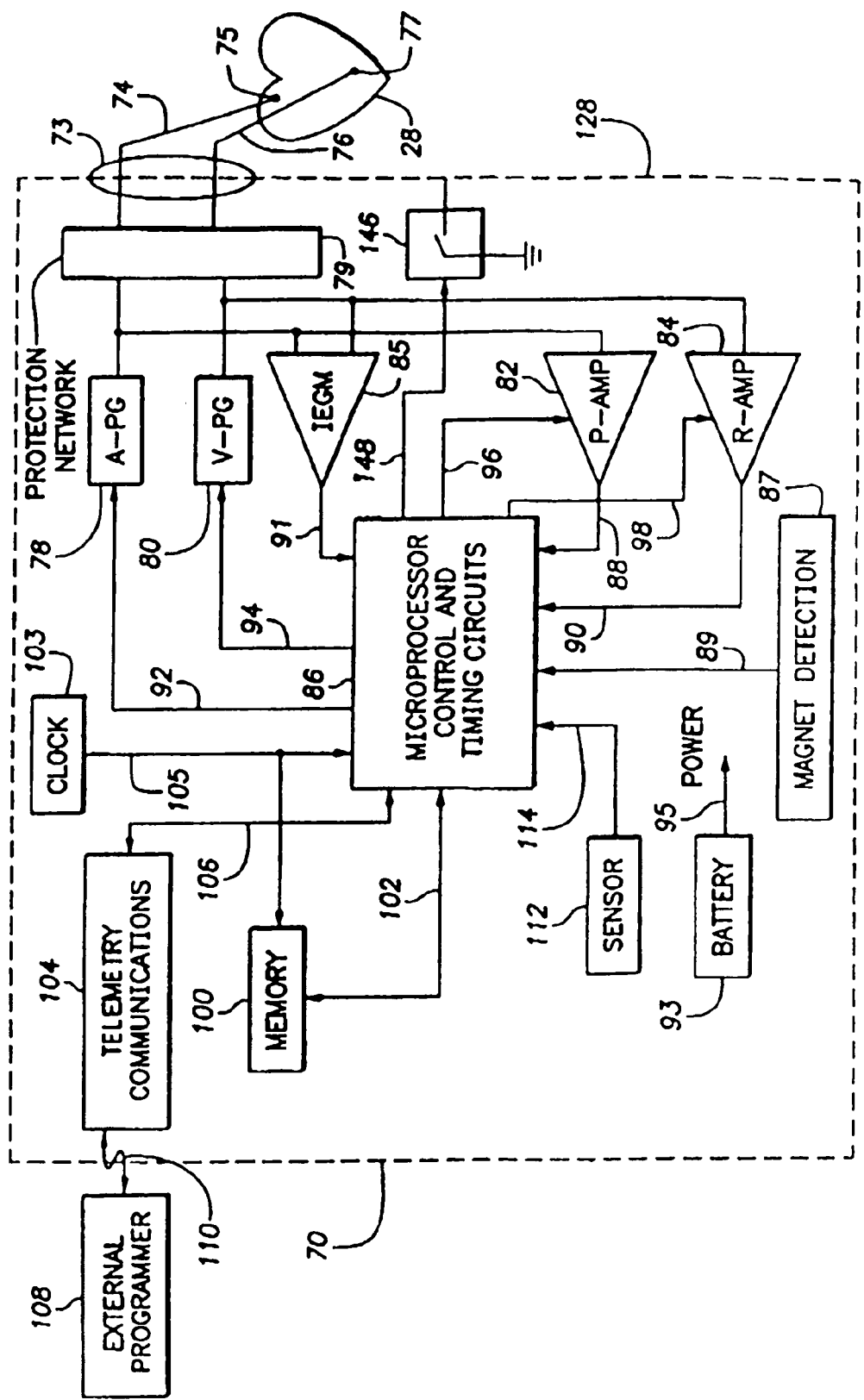
FIG. 3 shows a functional block diagram of an implantable dual-chamber pacemaker, which represents another type of implantable stimulation device with which the invention may be used.

In FIG. 2, there is shown a simplified functional block diagram of an ICD device 20, and in FIG. 3, there is shown a simplified functional block diagram of a dual-chamber pacemaker 70. It should also be noted that in some instances the functions of an ICD and a pacemaker may be combined within the same cardiac stimulation device. However, for teaching purposes, the devices will be described as separate cardiac stimulation devices.

It is the primary function of an ICD device to sense the occurrence of an arrhythmia, and to automatically apply an appropriate electrical shock therapy to the heart aimed at terminating the arrhythmia. To this end, the ICD device 20, as shown in the functional block diagram of FIG. 2, includes a control and timing circuit 22, such as a microprocessor, state-machine or other such control circuitry, that controls a high output charge generator 26. The high output charge generator 26 generates electrical stimulation pulses of moderate or high energy (corresponding to cardioversion or defibrillation pulses, respectively), e.g., electrical pulses having energies of from 1 to 10 joules (moderate) or 11 to 40 joules (high), as controlled by the control/timing circuit 22.

Such moderate or high energy pulses are applied to the patient's heart 28 through at least one lead 30 having at least two defibrillation electrodes, such as coil electrodes 38 and 40. The lead 30 preferably also includes at least one electrode for pacing and sensing functions, such as electrode 32. Typically, the lead 30 is transvenously inserted into the heart so as to place the coil electrodes 38 and 40 in the apex of the heart and in the superior vena cava, respectively. While only one lead is shown in FIG. 2, it is to be understood that additional defibrillation leads and electrodes may be used as desired or needed in order to efficiently and effectively apply the shock treatment generated by the high voltage generator 26 to the patient's heart 28.

The ICD 20 also includes a sense amplifier 42 that is coupled to at least one sensing electrode 32. It is the function of the sense amplifier 42 to sense the electrical activity of the heart 28, as is known in the art, such as R-waves which occur upon the depolarization, and hence contraction, of ventricular tissue; and P-waves which occur upon the depolarization, and hence contraction, of atrial tissue. Thus, by sensing R-waves and/or P-waves through the sense amplifier 42, the control/timing circuit 22 is able to make a determination as to the rate and regularity of the patient's heart beat. Such information, in turn, allows the control/timing circuit 22 to determine whether the heart 28 of a patient is experiencing an arrhythmia, and to apply appropriate stimulation therapy. Alternatively, a pacing pulse generator 43 can be used to periodically drive electrode 42 to maintain heart operation.

The control/timing circuit 22 further has a memory circuit 44 coupled thereto wherein the operating parameters used by the control/timing circuit 22 are stored. Such operating parameters define, for example, the amplitude of each shock energy pulse to be delivered to the patient's heart 28 within each for of therapy, as well as the duration of these shock pulses. The memory 44 may take many forms, and may be subdivided into as many different memory blocks or sections (addresses) as needed to store desired data and control information. A feature of an exemplary ICD 20 is the ability to sense and store a relatively large amount of data as a data record, which data record may then be used to guide the operation of the device, i.e., the present operating mode of the device may be dependent, at least in part, on past performance data.

Advantageously, the operating parameters of the implantable device 20 may be non-invasively programmed into the memory 44 through a telemetry circuit 46, in telecommunicative contact with an external programmer 48 by way of a suitable coupling coil 50. The coupling coil 50 may serve as an antenna for establishing a radio frequency (RF) communication link 52 with the external programmer 48, or the coil 50 may serve as a means for inductively coupling data to and from the telemetry circuit 46 from and to the external programmer 48, as is known in the art. See, e.g., U.S. Pat. No. 4,809,697 (Causey, III et al.) and U.S. Pat. No. 4,944,299 (Silvian), incorporated herein by reference. Further, such telemetry circuit 46 advantageously allows status information relating to the operation of the ICD 20, as contained in the control/timing circuit 22 or memory 44, to be sent to the external programmer 48 through the established link 52.

The control/timing circuit 22 includes appropriate processing and logic circuits for analyzing the output of the sense amplifier 42 and determining if such signals indicate the presence of an arrhythmia. Typically, the control/timing circuit 22 is based on a microprocessor, or similar processing circuit, which includes the ability to process or monitor input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that performs the functions described herein. The use, design, and operation of microprocessor-based control circuits to perform timing and data analysis functions is known in the art.

The ICD 20 additionally includes a battery 62 which provides operating power to all of the circuits of the ICD 20.

In FIG. 3, a simplified block diagram of the circuitry needed for a dual-chamber pacemaker 70 is illustrated. The pacemaker 70 is coupled to a heart 28 by way of leads 74 and 76, the lead 74 having an electrode 75 that is in contact with one of the atria of the heart, and the lead 76 having an electrode 77 that is in contact with one of the ventricles of the heart. The leads 74 and 76 are electrically and physically connected to the pacemaker 70 through a connector 73 that forms an integral part of the housing wherein the circuits of the pacemaker are housed. Typically, leads 74 and 76 are operated in a bipolar mode where a "tip" portion provides the voltage signal that provides current that flows to a "ring" portion on the same lead. Alternatively, leads 74 and 76 can operate in a unipolar mode where current flows from the "tip" portion of each lead to a conductive case 128 which surrounds the pacemaker device 70.

The connector 73 is electrically connected to a protection network 79, which network 79 electrically protects the circuits within the pacemaker 70 from excessive shocks or voltages that could appear on the electrodes 75 and/or 77 in the event such electrodes were to come in contact with a high voltage signal, e.g., from a defibrillation shock.

The leads 74 and 76 carry stimulation pulses to the electrodes 75 and 77 from an atrial pulse generator (A-PG) 78 and a ventricular pulse generator (V-PG) 80, respectively. Further, electrical signals from the atria are carried from the electrode 75, through the lead 74, to the input terminal of an atrial channel sense amplifier (P-AMP) 82; and electrical signals from the ventricles are carried from the electrode 77, through the lead 76, to the input terminal of a ventricular channel sense amplifier (R-AMP) 84. Similarly, electrical signals from both the atria and ventricles are applied to the inputs of an intracardiac electrogram amplifier (IEGM) 85. The amplifier 85 Is typically configured to detect an evoked response from the heart 28, i.e., a response to an applied stimulation pulse, thereby aiding in the detection of "capture". (Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.) Following each captured stimulation pulse, the associated cardiac tissue (i.e., the atria or the ventricles) enters into a refractory period when it cannot be restimulated.

The dual-chamber pacemaker 70 is controlled by a control system 86 that typically includes a microprocessor programmed to carry out control and timing functions. The control system 86 receives the output signals from the atrial (P-AMP) amplifier 82 over signal line 88. Similarly, the control system 86 receives the output signals from the ventricular (R-AMP) amplifier 84 over signal line 90, and the output signals from the IEGM amplifier 85 over signal line 91. These output signals are generated each time that an intrinsic P-wave or an R-wave or an evoked response is sensed within the heart 28. As with each evoked response, the cardiac tissue enters into a refractory period following each intrinsic P-wave or R-wave during which time period the associated cardiac tissue, i.e., the atria or the ventricles, cannot be restimulated. The control system 86 also generates trigger signals that are sent to the atrial pulse generator (A-PG) 78 and the ventricular pulse generator (V-PG) 80 over signal lines 92 and 94, respectively, to control the amplitude and duration of the signals delivered to the electrodes, 73 and 77. These trigger signals are generated each time that a stimulation pulse is to be generated by the respective pulse generator 78 or 80. The atrial trigger signal is referred to simply as the "A-trigger", and the ventricular trigger signal is referred to as the "V-trigger".

During the time that either an A-pulse or V-pulse is being delivered to the heart, the corresponding amplifier, P-AMP 82 and/or R-AMP 84, is typically disabled by a blanking signal presented to these amplifiers from the control system over signal lines 96 and 98, respectively. This blanking action prevents the amplifiers 82 and 84 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

As shown in FIG. 3, the pacemaker 70 further includes a memory circuit 100 that is coupled to the control system 86 over a suitable data/address bus 102. This memory circuit 100 allows certain control parameters, used by the control system 86 in controlling the operation of the pacemaker, to be programmably stored and modified, as required, in order to customize the pacemaker's operation to suit the needs of a particular patient. Further, data sensed during the operation of the pacemaker may be stored in the memory 100 for later retrieval and analysis.

As with the memory 44 of the ICD device 20 shown in FIG. 2, the memory 100 of the pacemaker 70 (FIG. 3) may take many forms, and may be subdivided into as many different memory blocks or sections (addresses) as needed in order to allow desired data and control information to be stored. A feature of an exemplary cardiac stimulation device is the ability to store a relatively large amount of sensed data as a data record, which data record may then be used to guide the operation of the device. That is, the operating mode of the pacemaker may be dependent, at least in part, on past performance data. For example, an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course, in addition to (or in lieu of) atrial rate, may be similarly sensed, stored, averaged (or otherwise processed), and then used for comparison purposes against one or more currently-sensed parameters. Advantageously, modem memory devices allow for the storage of large amounts of data in this manner.

A clock circuit 103 directs an appropriate clock signal(s) to the control system 86, as well as to any other needed circuits throughout the pacemaker 70 (e.g., to the memory 100) by way of clock bus 105.

A telemetry/communications circuit 104 is further included in the pacemaker 70. This telemetry circuit 104 is connected to the control system 86 by way of a suitable command/data bus 106. In turn, the telemetry circuit 104, which is included within the implantable pacemaker 70, may be selectively coupled to an external programmer 108 by means of an appropriate communication link 110, which communication link 110 may be any suitable electromagnetic link, such as an RF (radio frequency) channel, a magnetic link, an inductive link, an optical link, and the like. Advantageously, through the external programmer 108 and the communication link 110, desired commands may be sent to the control system 86. Similarly, through this communication link 110 with the programmer 108, data commands (either held within the control system 86, as in a data latch, or stored within the memory 100) may be remotely received from the programmer 108. Similarly, data initially sensed through the leads 74 or 76, and processed by the microprocessor control circuits 86, or other data measured within or by the pacemaker 70, may be stored and uploaded to the programmer 108. In this manner, non-invasive communications can be established with the implanted pacemaker 70 from a remote, non-implanted, location.

The pacemaker 70 additionally includes a battery 93 which provides operating power to all of the circuits of the pacemaker 70 via a power signal line 95.

It is noted that the pacemaker 70 in FIG. 3 is referred to as a dual-chamber pacemaker because it interfaces with both the atria and the ventricles of the heart 77. Those portions of the pacemaker 70 that interface with the atria, e.g., the lead 74, the P-wave sense amplifier 82, the A-PG 78, and corresponding portions of the control system 86, are commonly referred to as the "atrial channel". Similarly, those portions of the pacemaker 70 that interface with the ventricles, e.g., the lead 76, the R-wave sense amplifier 84, the V-pulse generator 80, and corresponding portions of the control system 86, are commonly referred to as the "ventricular channel".

As needed for certain applications, the pacemaker 70 may further include at least one sensor 112 that is connected to the control system 86 of the pacemaker 70 over a suitable connection line 114. While this sensor 112 is illustrated in FIG. 3 as being included within the pacemaker 70, it is to be understood that the sensor may also be external to the pacemaker 70, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, pH of blood, body motion, and the like. The type of sensor used is not critical to the present invention. Any sensor or combination of sensors capable of sensing a physiological or physical parameter relatable to the rate at which the heart should be beating (i.e., relatable to the metabolic need of the patient), and/or relatable to whether a tachyarrhythmia is likely to soon occur, can be used. Such sensors are commonly used with "rate-responsive" pacemakers in order to adjust the rate (pacing cycle) of the pacemaker in a manner that tracks the physiological or metabolic needs of the patient.

The pacemaker 70 further includes magnet detection circuitry 87, coupled to the control system 86 over signal line 89. It is the purpose of the magnet detection circuitry 87 to detect when a magnet is placed over the pacemaker, which magnet may be used by a physician or other medical personnel to perform various reset functions of the pacemaker 70, and/or to signal the control system 86 that an external programmer 108 is in place to receive data from, or send data to, the pacemaker memory 100 or control system 86 through the telemetry communications circuits 104.

As with the ICD device 20 of FIG. 2, the telemetry or communications circuit 104 may be of conventional design, such as is described in U.S. Pat. No. 4,944,299, or as is otherwise known in the art. Similarly, the external programmer 108 may be of any suitable design known in the art, such as is described in U.S. Pat. No. 4,809,697. Likewise, the memory circuit 100, and the circuits utilized in the atrial and ventricular channels may all be of common design as is known in the pacing art. The present invention is not concerned with the details of the circuitry utilized for each of these pacing elements. Rather, it is concerned with the manner in which infection control signals are generated in coordination with a particular pacing mode of operation. Such coordination is controlled by the control system 86.

The control system 86 may be realized using a variety of different techniques and/or circuits. The preferred type of control system 86 ~s a microprocessor-based control system. It is noted, however, that the control system 86 could also be realized using a state machine. Indeed, any type of control circuit or system could be employed for the control system 86. The present invention is likewise not concerned with the details of the control systems 22 and 86. Rather, it is concerned with the end result achieved by the control system. That is, so long as the control system 86 controls the operation of the pacemaker (or other medical device) so that the desired functions are achieved as set forth herein, it matters little what type of control system is used. Those of skill in the implantable medical device art, given the teachings presented herein, should thus be able to fashion numerous different types of control systems or circuits that achieve the desired device control.

Representative of the types of control systems that may be used with the invention is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are incorporated herein by reference.

Figure 4:
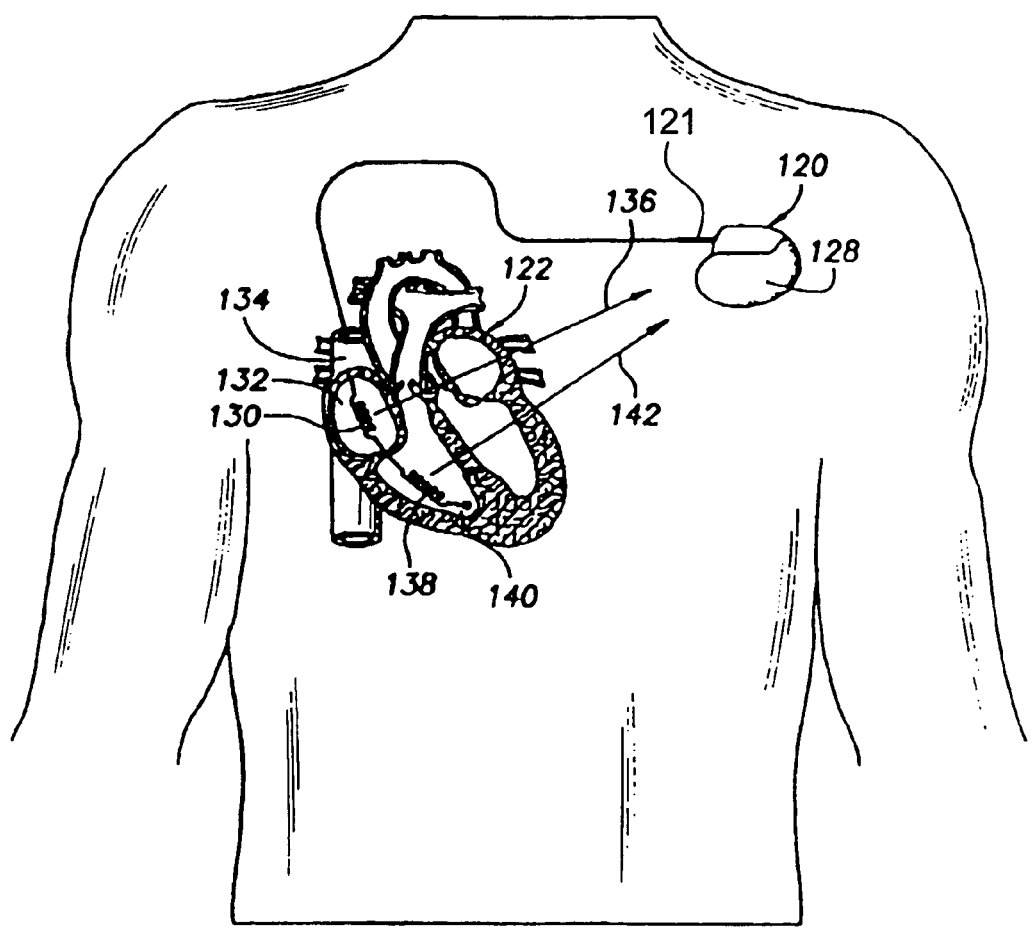
FIG. 4 is a diagrammatic illustration of an implanted cardiac stimulation device in combination with a pectoral implant embodying the invention including one electrode In the region of the right atrium and another electrode in the right ventricle.

Referring to FIG. 4, there is shown a diagrammatic illustration of an implanted cardiac stimulation device 120 (e.g., an ICD 20 or pacemaker 70) in combination with a pectoral implant embodying the invention including one electrode 130 in the region of the right atrium and another electrode 138 in the right ventricle of a patient's heart 122. As earlier noted, microorganisms may form in a biofilm on surfaces of a housing 128 of the implanted cardiac stimulation device 120. Prior to the present invention, bacterial infections in the biofilm have been relatively untreatable without device removal since the bacteria live in the device's biofilm. The biofilm protects the bacteria from systemic antibiotics, allowing them to tolerate levels of antibiotics that are several orders of magnitude above that which can safely be given a patient In order to treat these infections, embodiments of the present invention use at least one electrode 130, the SVC electrode (e.g., a wire coil), which is electrically connected to the implanted cardiac stimulation device 120. The electrode 130 is implanted within the heart 122 within the region of the right atrium 132, preferably within the superior vena cava 134, leading into the right atrium 132. A first electrical current generator, e.g., the atrial pulse generator (A-PG) 78, is operable to deliver an electrical current to the electrode 130 which flows (as indicated by arrow 136) to the conductive housing 128 of the implanted cardiac stimulation device 120 in such a manner that bacteria residing in a biofilm on the implanted cardiac stimulation device 120 are destroyed. In one instance, the electrical current generator periodically generates a D.C. electrical current during the heart's refractory period. In another instance, the electrical current generator generates a high-speed square wave electrical current in a frequency range which is too rapid to affect the heart 122.

In another embodiment, a second electrode 138, the RV electrode, is electrically connected to a second electrical current generator, e.g., the ventricular pulse generator (V-PG) 80, but is instead implanted within the right ventricle 140 of the heart 122. In this instance, the first electrical current generator is operable to deliver a first electrical current to the first electrode 130 which flows (as indicated by arrow 136) to the housing 128 of the implanted cardiac stimulation device 120 following the P-wave portion of the intracardiac electrogram for the heart such that arrhythmo-genesis or parasitic pacing will not occur in the atrium. Additionally, the second electrical current generator is operable to deliver a second electrical current to the second electrode 138 which flows (as indicated by arrow 142) to the housing 128 of the implanted cardiac stimulation device 120 following the R-wave portion of the Intracardiac electrogram such that arrhythmo-genesis or parasitic pacing will not occur in the right ventricle 40. By so operating (preferably in combination with a biocide), bacteria residing in a biofilm on the implanted cardiac treatment device 120 are destroyed.

To obtain maximum therapeutic benefit, an average current density of about 150 microamperes per square centimeter is preferably applied to the housing 128 for a duration of about 10 hours. However, as discussed previously, this current density requires approximately a 10 ma current flow to the housing 128, a current that could pace the heart or induce an arrhythmia. Accordingly, the present invention describes two primary embodiments for dealing with this problem.

Figure 5:
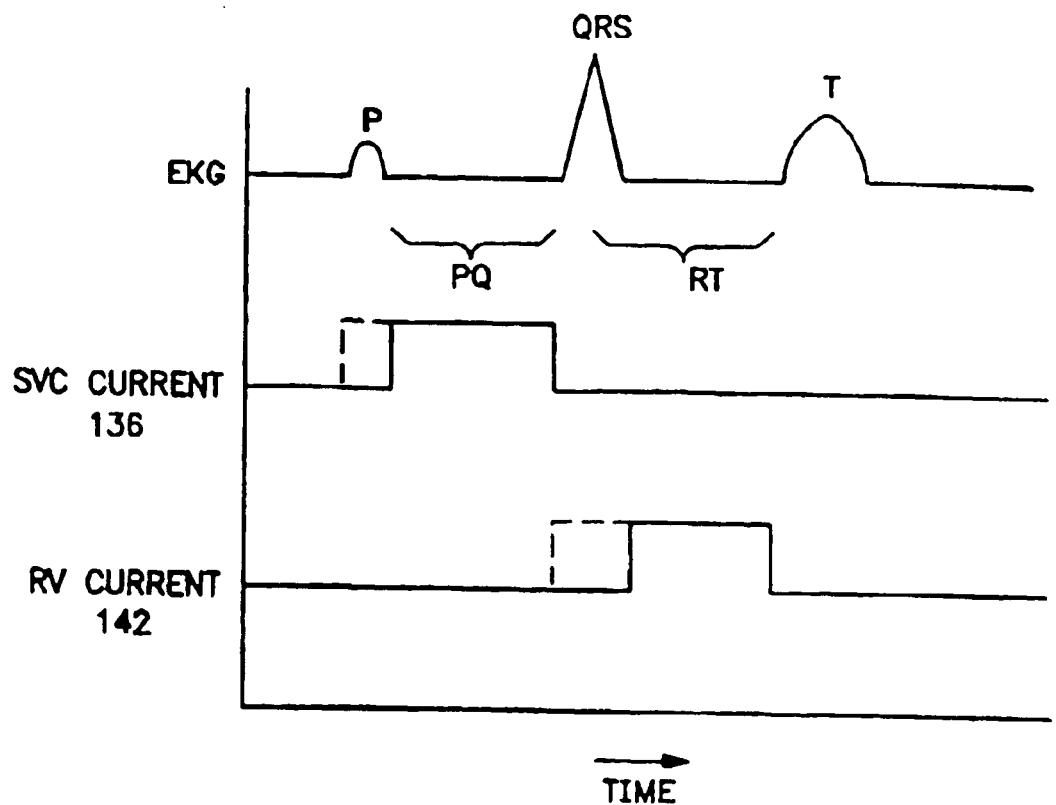
FIG. 5 is an electrogram with indications, according to the invention, of electrical currents from the electrode in the region of the atrium and from the electrode in the ventricle wherein the electrical infection control currents are supplied during refractory periods.

The first embodiment for solving this problem is illustrated in FIG. 5. In this first embodiment, the SVC current 136 (that is, current to electrode 130) is periodically delivered during the refractory period of the right atrium, preferably during the period of time between the P and Q wave portions of the illustrated electrogram (designated as the PQ segment). Similarly, the RV current 142 (that is current to electrode 138) is periodically delivered during the refractory period of the right ventricle, preferably during the period of time between the R and T wave portions of the illustrated electrogram (designated as the RT segment). Since the SVC current 136 is delivered following the P-wave, which is after the atria have already begun to contract and have entered a refractory period, there will be no arrhythmo-genesis or parasitic pacing in the atrium 132. Similarly, since the RV current 142 will be delivered following the R-wave, which is after the ventricles have already begun to contract and have likewise entered a refractory period, there will be no arrhythmo-genesis or parasitic pacing in the right ventricle 140. While the potential for a high ventricular field generating a premature pacing event in the atria does exist, this is not considered a serious side effect.

Alternatively, one could asynchronously drive the RV coil with ventricular pulses at a moderately high rate above the normal pacing rate for the patient's heart, e.g., 80 bpm, to force pacing of the patient's heart and thus there would be no need to sense R-waves. Accordingly, the timing for the infection control current pulses on the RV coil in such a VOO mode could be derived from the timing of the ventricular pulses. Similarly, an AOO mode could be used for generating infection control current pulses on the SVC coil or a DOO mode could be used for generating infection control pulses on both the SVC and RV coils. In an alternative implementation, the timing for the infection control pulses could be determined by sensing evoked P and R-wave responses to the associated pacing pulses.

FIG. 5 shows an exemplary waveform of the infection control current (solid portion) emitted by a device of the present invention when the cardiac stimulation device 120 is not generating stimulation pulses, i.e., when the heart 122 is beating within programmed limits of the cardiac stimulation device 120. In this mode, the sense amplifiers, e.g., 82 and 84, detect intrinsic P and R-waves, and this detection is used to determine the refractory period of the associated cardiac tissue, i.e., the atria or the ventricles, during which time period the associated infection control current is provided. Preferably, the associated pulse generator, e.g., 78 or 80, can be used to provide the infection control current. Alternating between the SVC and RV leads provides the additional benefit that the average current density around the device housing 128 will be slightly more homogeneous. When, pacing pulses are required (see dotted line portions), they precede the infection current pulses (from the SVC 136 and RV 142 currents) and are used to stimulate the heart as described in reference to FIG. 3. In this mode, the control system 86 can extend the stimulation pulses to the atria or ventricles, e.g., to a duration of greater than 10 ms but less than approximately 300 ms, such that the associated pulse generator, e.g., 78 or 80, can also provide the infection control current. Accordingly, the stimulation pulses will extend into the associated the refractory periods of the atria and ventricles and thus also function as current control pulses. Preferably, the same infection control apparatus can operate in both of the aforementioned modes, dependent upon whether intrinsic P and R-waves were detected during each cardiac cycle.

Figure 6:
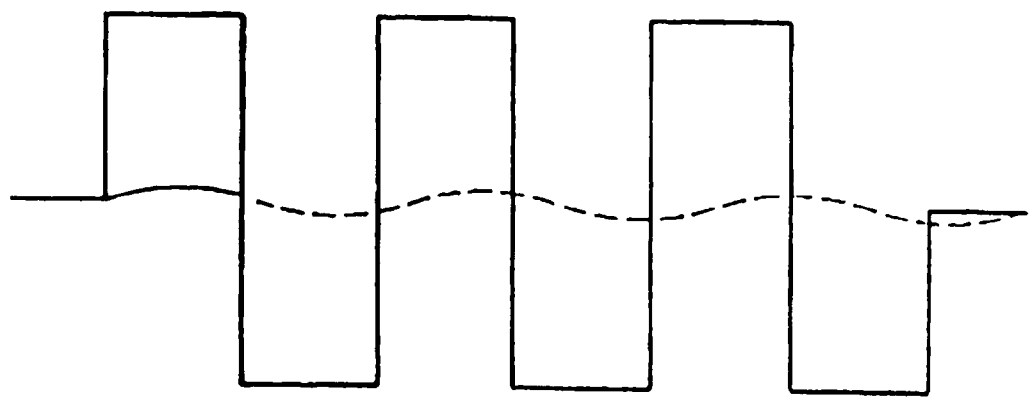
FIG. 6 illustrates a high-speed square wave generated from the electrodes to the housing of the cardiac stimulation device and the resulting response by the heart cells wherein the square wave is supplied at a frequency that is too high to significantly stimulate the heart.

FIG. 6 shows an alternate embodiment. In this embodiment, a high-speed square wave (shown as a solid line) is generated by pulse generators 78, 80 and preferably generates an oscillating output through each of the electrodes 130, 138 to the housing 128. Using a frequency of approximately 1–10 kHz, the pulsing is too rapid to be "felt" by the heart cells due to their slow membrane time constant response (shown as a dashed line), i.e., the heart muscles will not be stimulated by this signal. However, this higher frequency alternating current will still enhance the efficacy of the antibiotics against the biofilm.

Preferably, the present invention uses the same circuitry and leads that are already a portion of an existing cardiac stimulation device. For example, when the present invention is implemented with a pacemaker 70 (FIG. 3), electrode 75 is used as the SVC electrode 130 and electrode 77 is used as the RV electrode 138. For pacemakers operating in a unipolar mode, these leads can be driven in their normal manner and with voltage levels similar to those used for unipolar stimulation (e.g., approximately 3–9 volts). For pacemakers that are implemented in a bipolar mode, i.e., in a mode where each electrode lead includes a "tip" and a "ring" (return connection), the present invention additionally includes a circuit 146 (see FIG. 2) under control of the control system 86 using signal 148 to periodically ground casing 128 during the aforementioned refractory periods when this infection control mode is activated to enable a voltage signal (e.g., 3–9 volts) generated at the "tip" electrode to cause a treatment current (e.g., averaging approximately 10 ma) to flow to the casing 128 in a manner similar to a unipolar mode. Additionally, the control system 86 is used to generate the timing, corresponding to the refractory periods, as shown in FIG. 5. The control system 86 uses any of the following sense amplifiers, P-AMP 82, R-AMP 64 and IEGM 85, to sense signals from the heart and thereby identify the refractory periods. The control system 86 then generates infection control signals by using this information to control any of the following pulse generators, A-PG 78 and V-PG 80, to generate programmable amplitude signals within these refractory periods. Similarly, the ICD 20 can use electrode 38 as the SVC electrode 130 and the pace generator 43 under control of the control and timing circuit 22 to generate the described infection control current during the aforementioned refractory period. Furthermore, the ICD 20 can be modified to include circuitry to generate SVC and RV infection control currents.

Preferably, the above-described infection control is implemented for a period of time, e.g., 10 hours, under command from an external programmer (e.g., 48, 108 as described in reference to FIGS. 2 and 3). Actually, the treatment time is preferably extended to adjust for the combined duty cycle of the SVC and RV currents since even this combined duty cycle is still less than 100%. Alternatively, the voltage levels output by the A-PG 78 and V-PG 80 can be upwardly adjusted to accommodate for the reduced duty cycle.

In a first operational mode, this infection control mode is activated when symptoms of an infection first develop. Preferably, this infection control mode is combined with a systemic course of antibiotics, typically supplied either orally or by injection to the entire body. Due to the desired current density and treatment duration, use of the infection control mode can use a significant portion of the battery life (10 ma*10 hours=10 ma-hrs) of a typical device, e.g., approximately 10%. Accordingly, it may be desirable to use this mode only when symptoms develop. Alternatively, in a second operational mode, the infection control mode is activated soon after implantation, e.g., after initial adjustments of pacing voltage threshold levels. This second operational mode may be desirable to prophylactically avoid infections since a course of antibiotics is a normal practice following implantation surgery. Furthermore, a biocide may be additionally be supplied at the site of the implantation, e.g., surrounding the cardiac stimulation device. In this operational mode, infections may be avoided altogether (at the expense of the overall battery life of the device).

It should also be noted that in case the housing includes a separate connector top or header for connecting electrode leads to the housing as is well known in the art, for instance of the kind made of epoxy resin and molded onto the housing, the surface should be covered with a conductive coating that is in contact with the electrical current generator, directly or via the housing.

In a preferred embodiment the proximate part of the surface of the lead is conductive and is capable of being coupled to the electrical current generator. This proximate part 121 should extend to a position from the housing which, after implantation, is situated at a location beyond the entry of the lead into the venous system and the entry into the into superior vena cava. In this way the infection control may also be extended to the proximal parts of the lead. This may for instance be achieved by means of an electrically conducting polymer applied on said exterior surfaces of the proximal part of the lead (and also on said possible connector top). In this way conventionally non-conducting surfaces of a heart stimulator are made electrically conductive. An example of a polymer suitable for this purpose is an electrically conducting polymer marketed under the trademark ELASTOSIL.

Alternatively an electrically conducting coil can be applied around the proximal part of the lead. In this way the proximal part of the lead is made not only electrically conductive but the wear resistance of the lead is improved.

The exterior surfaces of the proximal part of the lead and of the connector top (if present) may alternatively be treated by ion implantation technology or so-called Ion-Beam-Assisted-Deposition. This technique is especially well suited for making stimulator connector tops or headers of epoxy electrically conductive.

Other possible technologies to make a surface conducting are Physical Vapor Deposition, PVD, or Chemical Vapor Deposition, CVD or any sputtering process.

If the housing is not made of an electrically conducting material, any of the above methods may of course be used in order to make the housing conductive.

It has been found that oxide layers, especially titanium oxide layers but also other metal oxide layers may be formed when such metals are used in the DC current environment dealt with in conjunction with the present invention. These oxide layers may cause an uneven current distribution possibly detrimental to the infection control effect. The current may also be lowered due to increased impedance caused by the oxide layer to a point at which the effect on bacteria in the biofilm is no longer effective. The formation of such oxide layers is avoided, according to an advantageous embodiment of the apparatus according to the invention, by coating the generator housing and other metallic surfaces that may become oxidized due to the DC current with one of the metals platinum, palladium or iridium or any other metal with similar electrochemical characteristics or an alloy of these metals.

While preferred embodiments of the invention have been disclosed in detail, it should be understood by those skilled in the art that various other modifications may be made to the illustrated embodiments without departing from the scope of the invention as described in the specification and defined in the appended claims. For example, implementations using atrial SVC or ventricle RVC leads alone or in any combination are considered to be within the scope of the present invention. Furthermore, while it is desirable to use the same circuitry and control leads as an implanted cardiac stimulator to generate the infection control currents, implementations which use additional leads and circuitry to generate the aforedescribed infection control currents are also considered to be within the scope of the present invention.

The invention claimed is:

1. A cardiac stimulating device comprising:
   a pulse generator for generating a stimulation pulse adapted to stimulate the heart of a subject;
   detection circuitry for determining a refractory period following stimulation of the heart;
   a housing, adapted for implantation in the subject, said housing containing said pulse generator circuitry and said detection circuitry, and having an exterior surface that is entirely electrically conductive;
   an electrode lead connected to said housing and carrying an electrode adapted for implantation in the heart and having a proximal portion with an electrically conductive surface thereon, said electrically conductive surface extending substantially from said housing to a location, after implantation, situated after entry of the electrode lead into the venous system and before entry of the electrode lead into the superior vena cava, said proximal portion having an exterior with an electrically conductive surface thereon;
   said pulse generator comprising current generating circuitry electrically connected to said electrode;
   a normally open switch in said housing connected between said current generating circuitry and said exterior surface of said housing; and
   a controller in said housing connected to said detection circuitry and to said switch for closing said switch only at a time encompassed by said refractory period to complete a circuit including said current generating circuitry, said exterior surface of said housing, said electrode and said electrically conductive surface at the exterior of said proximal portion of said electrode lead, for an infection control current generated by said current generating circuitry to counteract bacterial growth at least at said exterior surface of said housing.

2. A cardiac stimulating device as claimed in claim 1 wherein said electrode carried by said electrode lead is electrically connected to said pulse generator, and is adapted to deliver said stimulation pulse to the heart.

3. A cardiac stimulating device as claimed in claim 2 wherein said electrode carried by said electrode lead also is electrically connected to said detection circuitry and is adapted to sense cardiac electrical activity of the heart for use by said detection circuitry for determining said refractory period.

4. A cardiac stimulating device as claimed in claim 1 wherein said electrode carried by said electrode lead is a first electrode adapted for implantation in the right atrium of the heart, and further comprising a second electrode carried by said electrode lead and adapted for implantation in the right ventricle of the heart, and wherein said current generating circuitry comprises a first current generator connected to said first electrode and a second current generator connected to said second electrode, and wherein said detection circuitry comprises a first sense amplifier connected to said first electrode for detecting a refractory period of the right atrium, and a second sense amplifier connected to the second electrode for detecting a refractory period of the right ventricle, and wherein said controller operates said first and second current generators to cause a first infection control current to flow during the refractory period of the right atrium in a circuit including said first current generator, said exterior surface of said housing, said first electrode and said electrically conductive surface at the exterior of said proximal portion of the electrode lead, and for causing a second infection current to flow during the refractory period of the right ventricle in a circuit including said second current generator, said exterior surface of said housing, said second electrode and said electrically conductive surface at the exterior of said proximal portion of the electrode lead.

5. A cardiac stimulating device as claimed in claim 1 wherein said electrode carried by said electrode lead is adapted for implantation in the right atrium of the heart, and wherein said detection circuitry includes a sense amplifier electrically connected to said electrode for detecting a refractory period of the right atrium by sensing an intrinsic P-wave via said electrode.

6. A cardiac stimulating device as claimed in claim 1 wherein said electrode carried by said electrode lead is adapted for implantation in the right atrium of the heart, and wherein said detection circuitry includes a sense amplifier electrically connected to said electrode for detecting a refractory period of the right atrium by sensing an evoked P-wave via said electrode.

7. A cardiac stimulating device as claimed in claim 1 wherein said electrode carried by said electrode lead is adapted for implantation in the right ventricle of the heart, and wherein said detection circuitry includes a sense amplifier electrically connected to said electrode for detecting a refractory period of the right atrium by sensing an intrinsic R-wave via said electrode.

8. A cardiac stimulating device as claimed in claim 1 wherein said electrode carried by said electrode lead is adapted for implantation in the right ventricle of the heart, and wherein said detection circuitry includes a sense amplifier electrically connected to said electrode for detecting a refractory period of the right atrium by sensing an evoked R-wave via said electrode.

9. A cardiac stimulating device as claimed in claim 1 wherein said deflection circuitry is connected to said generator circuitry, and determines said refractory period by timing a period following generation of said stimulation pulse.

10. A cardiac stimulating device as claimed in claim 1 wherein said pulse generating circuitry comprises pacing pulse generator for generating a pacing pulse as said stimulation pulse.

11. A cardiac stimulating device as claimed in claim 10 wherein said electrode lead is electrically connected to said pulse generating circuitry, and comprises a bipolar electrode arrangement that includes said electrode.

12. A cardiac stimulating device as claimed in claim 1 wherein said pulse generating circuitry comprises defibrillation pulse generator for generating a defibrillation pulse as said stimulation pulse.

13. A cardiac stimulating device as claimed in claim 1 wherein said pulse generator comprises cardioversion pulse generating circuitry for generating a cardioversion pulse as said stimulation pulse.

14. A cardiac stimulating device comprising:
   a housing, adapted for implantation in a subject, containing stimulation circuitry adapted to electrically stimulate the heart of the subject, said housing having an external surface which is entirely electrically conductive;
   an electrode lead connected to said housing and carrying an electrode adapted for implantation in the heart and having a proximal portion with an electrically conductive surface thereon said electrically conductive surface extending substantially from the housing to a location, after implantation, situated beyond entry of the electrode lead into the venous system and before entry of the electrode lead into the superior vena cava;

a current generator contained in said housing which generates a current having a square waveform; and a control unit contained in said housing for operating said current generator and that temporarily completes a circuit for said current including said exterior surface of said housing, said electrode and said electrically conductive surface at the exterior of said proximal portion of said electrode lead, for an infection control current to counteract bacterial growth at least at said exterior surface of said housing.

15. A cardiac stimulating device as claimed in claim 14 wherein said housing comprises a connector top, to which said electrode lead is mechanically and electrically connected, said connector top having an externally electrically conductive surface that is included in said circuit completed by said control unit.

16. A cardiac stimulating device as claimed in claim 15 wherein at least one of said electrically conductive surface on said exterior of said proximal portion of said electrode lead and said electrically conductive external surface of said connector top is formed by an electrically conductive polymer.

17. A cardiac stimulating device as claimed in claim 15 wherein at least one of said electrically conductive surface on said exterior of said proximal portion of said electrode lead and said electrically conductive external surface of said connector top is formed by an ion implantation.

18. A cardiac stimulating device as claimed in claim 15 wherein at least one of said electrically conductive surface on said exterior of said proximal portion of said electrode lead and said electrically conductive external surface of said connector top is formed by an ion beam assisted deposition.

19. A cardiac stimulating device as claimed in claim 15 wherein at least one of said electrically conductive surface on said exterior of said proximal portion of said electrode lead and said electrically conductive external surface of said connector top is formed by a coating applied by a process selected from the group consisting of vapor deposition and sputtering.

20. A cardiac stimulating device as claimed in claim 14 wherein said current generator generates said current at a frequency in a range between 1 and 10 kHz.

21. A cardiac stimulating device as claimed in claim 14 wherein said stimulation circuitry comprises pacing circuitry.

22. A cardiac stimulating device as claimed in claim 14 wherein said stimulating circuitry comprises cardioversion circuitry.

23. A cardiac stimulating device as claimed in claim 14 wherein said stimulation circuitry comprises defibrillation circuitry.

24. A cardiac stimulating device as claimed in claim 14 wherein said electrically conductive surface on said exterior of said proximal portion of said electrode lead is formed by an electrically conductive coil.

25. A cardiac stimulating device as claimed in claim 14 wherein said exterior surface of said housing has at least a portion composed of a metal that oxidizes in a DC current environment, and comprising a coating covering said portion of said surface formed by a material selected from the group consisting of platinum, palladium, indium, platinum alloys, palladium alloys and indium alloys.

26. A method for infection control for an implanted medical device comprising the steps of:

implanting a medical device in a subject, said medical device having a housing with an entirely electrically conductive exterior surface, and an electrode lead connected to said housing carrying an electrode and having a proximal portion with an electronically conductive surface thereon, said electrically conductive surface extending, after implantation, substantially from said housing to a location situated beyond entry of the electrode lead into the venous system and before entry of the electrode lead into the superior vena cava;

generating an electrical current in said housing; and selectively completing a circuit for said electrical current including said exterior surface of said housing, said electrode, said electrically conductive surface at the exterior of said proximal portion of said electrode lead, and biofluid of the subject to counteract, with said electrical current, bacterial growth at least at said exterior surface of said housing.

27. A method as claimed in claim 26 comprising the additional step of introducing a biocide with said medical device into the subject at least in a region surrounding said housing.

28. A method as claimed in claim 26 comprising the additional step of administering an antibiotic to the subject.

29. A method as claimed in claim 26 wherein the step of selectively completing said circuit comprises extracorporeally remotely activating said current generator to generate said electrical current.

30. A method as claimed in claim 29 comprising the additional step of detecting an infection associated with implantation of said medical device in the subject, and remotely activating said current generator after detection of said infection.

31. A method as claimed in claim 26 wherein the step of selectively completing said circuit comprises prophylactically activating said current generator immediately after implanting said medical device.

32. A method as claimed in claim 26 comprising the additional step of determining a refractory period of the heart of the subject, and wherein the step of selectively completing said circuit comprises completing said circuit only at a time encompassed by said refractory period.

* * * * *